(12) United States Patent
Sueto et al.

(10) Patent No.: US 7,465,834 B2
(45) Date of Patent: Dec. 16, 2008

(54) IONIC LIQUIDS AND PROCESS FOR MANUFACTURING THE SAME

(75) Inventors: Kumiko Sueto, Gunma (JP); Miyuki Kasahara, Gunma (JP); Osamu Omae, Gunma (JP); Yuan Gao, Gunma (JP)

(73) Assignee: Kanto Denka Kogyo Co., Ltd., Tokyo (JP)

( * ) Notice: Subject to any disclaimer, the term of this patent is extended or adjusted under 35 U.S.C. 154(b) by 851 days.

(21) Appl. No.: 11/005,708

(22) Filed: Dec. 7, 2004

(65) Prior Publication Data

US 2005/0136332 A1  Jun. 23, 2005

(30) Foreign Application Priority Data

Dec. 19, 2003  (JP) .............................. 2003-421985

(51) Int. Cl.
*C07C 211/01* (2006.01)

(52) U.S. Cl. ...................... 564/463; 257/431; 320/166; 429/122

(58) Field of Classification Search .................. 564/463
See application file for complete search history.

(56) References Cited

U.S. PATENT DOCUMENTS

2007/0287869 A1  12/2007  Ignatyev et al.

OTHER PUBLICATIONS

Air and Moisture Stable Room Temperature Ionic Liquid as a Novel Electrolyte for Electrochemical Devices, by H. Matsumoto and Y. Miyazaki, Molten Salts, 2001, vol. 44, No. 1, pp. 7-18.

Highly Conductive Room Temperature Molten Salts Based on Small Trimethylalkylammonium Cations and Bis(trifluoromethylsulfonyl)imide, by H. Matsumoto et al, Chemistry Letters, 2000, vol. 8, pp. 922-923.

Preparation of Novel Room-Temperature Molten Salts by Neutralization of Amines, by Michiko Hirao et al, Journal of Electrochemical Society, 2000, vol. 147, pp. 4168-4172.

*Primary Examiner*—Brian J Davis
(74) *Attorney, Agent, or Firm*—Flynn, Thiel, Boutell & Tanis, P.C.

(57) ABSTRACT

Ionic liquids exhibit a stable liquid state even at low temperatures and have a good conductivity. The ionic liquids each contain an organic compound represented by the following formula (1) as a cation.

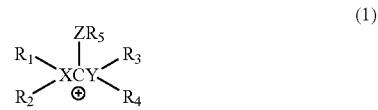

(1)

In the formula, $R_1$ to $R_5$ may be the same as or different from each other and each represents an H, a halogen, or a $C_1$ to $C_{10}$ alkyl group, cycloalkyl group, heterocyclic group, aryl group or alkoxyalkyl group; X and Y may be the same as or different from each other and each represents an N or a P; Z represents an S or an O.

20 Claims, No Drawings

IONIC LIQUIDS AND PROCESS FOR MANUFACTURING THE SAME

TECHNICAL FIELD

The present invention relates to ionic liquids that exhibit a liquid form over a broad temperature range from a low temperature region of or below room temperature, and a process for manufacturing such ionic liquids, and a lithium battery, a double layer capacitor and a dye-sensitized solar cell each using such an ionic liquid.

PRIOR ARTS

Ionic liquids formed with an onium containing an N such as an ammonium as a cation, many of which have been reported hitherto, exhibit a liquid form at temperatures above 20° C., but only a few of these exist in a liquid form at below 20° C., and hardly any maintain a stable liquid form at below 0° C. See H. Matsumoto and Y. Miyazaki, Yoyu-en oyobi Koon Kagaku (MOLTEN SALTS), 44, 7 (2001), H. Matsumoto, M. Yanagida, K. Tanimoto, M. Nomura, Y. Kitagawa and Y. Miyazaki, Chem. Lett, 8, 922 (2000) and M. Hirano, H. Sugimoto and H. Ohno, J. Electrochem. Soc., 147, 4168 (2000). This paucity of ionic liquids exhibiting a stable liquid form in a low temperature region is currently a big impediment to application as electrolytes or electrolyte additives for electrical storage devices such as lithium batteries, double layer capacitors or dye-sensitized solar cells.

DISCLOSURE OF THE INVENTION

It is a purpose of the present invention to provide ionic liquids, called also an ambient temperature molten salt, that exhibit a stable liquid state at below 20° C., preferably below 0° C., more preferably below −30° C., and have a good conductivity, and a process for manufacturing such ionic liquids, and furthermore it is a purpose to provide ionic liquids that can be used as materials in lithium batteries, double layer capacitors, dye-sensitized solar cells and so on; specifically, it is a purpose to provide novel methylium salts.

The present inventors have synthesized cations and then various salts (ionic liquids) comprising a cation, and carried out intensive studies into ionic liquids for solving the above problems, and as a result discovered that a salt containing an organic cation represented by the following formula (1) exhibits a liquid state at room temperature and has excellent conductivity, i.e. constitutes an ionic liquid.

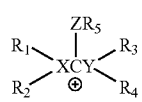

(1)

In the formula, $R_1$ to $R_5$ may be the same as or different from each other and each represents an H, a halogen, or a $C_1$ to $C_{10}$ (i.e. number of carbons from 1 to 10) alkyl group, cycloalkyl group, heterocyclic group, aryl group or alkoxyalkyl group; X and Y may be the same as or different from each other and each represents an N or a P; and Z represents an S or an O.

In other words the invention provides an ionic liquid comprising an organic compound represented by the above shown formula (1) as a cation. The invention provides an ionic liquid comprising a cation and an anion, wherein the cation comprises at least one selected from the group consisting of cations represented by the above shown formula (1).

The invention provides use of the organic compound above shown for an ionic liquid.

Then the invention provides a process for manufacturing the ionic liquid, including the step of reacting together an organic compound $R_5Q$ (wherein $R_5$ represents a $C_1$ to $C_{10}$ straight chain or branched alkyl group; and Q represents a halogen, $HSO_4$ or $NO_3$) and a compound represented by the following formula (2) (wherein, $R_1$ to $R_4$ may be the same as or different from each other and each represents an H, a halogen, or a $C_1$ to $C_{10}$ straight chain or branched alkyl group, cycloalkyl group, heterocyclic group, aryl group or alkoxyalkyl group; X and Y may be the same as or different from each other and each represents an N or a P; and Z represents an S or an O) in accordance with the following reaction scheme while stirring at 20 to 100° C., thus producing a salt represented by the formula (3).

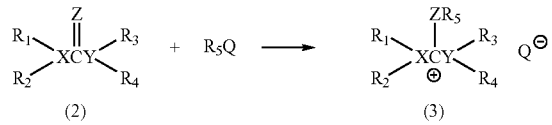

(2)                                    (3)

After the reaction step of the above shown process, the anion Q of the salt represented by the formula (3) and a compound AB (AB represents a compound selected from the group consisting of $LiN(CF_3SO_2)_2$, $NaN(CF_3SO_2)_2$, $KN(CF_3SO_2)_2$, $CF_3SO_3Li$, $CF_3SO_3Na$, $CF_3SO_3K$, $CF_3CH_2SO_3Li$, $CF_3CH_2SO_3Na$, $CF_3CH_2SO_3K$, $CF_3COOLi$, $CF_3COONa$, $CF_3COOK$, $LiPF_6$, $NaPF_6$, $KPF_6$, $LiBF_4$, $NaBF_4$, $KBF_4$, $LiSbF_6$, $NaSbF_6$, $KSbF_6$, $NaN(CN)_2$, $AgN(CN)_2$, $Na_2SO_4$, $K_2SO_4$, $NaNO_3$ and $KNO_3$) may be subjected to anion exchange through the reaction of the following reaction scheme, thus producing an ionic liquid represented by the formula (4).

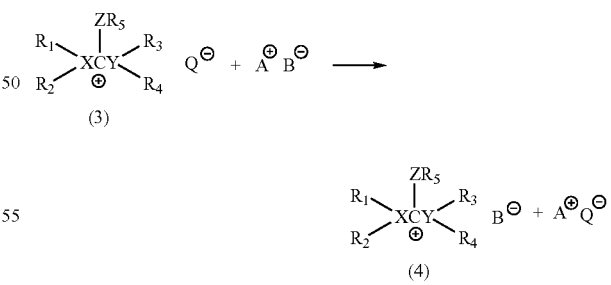

(3)

(4)

The invention provides use of the ionic liquid for a lithium battery, a double layer capacitor, a dye-sensitized solar cell or a green solvent. The invention provides a lithium battery, a double layer capacitor, a dye-sensitized solar cell or a green solvent, which includes the ionic liquid.

More specifically, such an ionic liquid is an ionic liquid comprising a cation and an anion, wherein the cation comprises at least one selected from the group consisting of cations represented by the following formula (1):

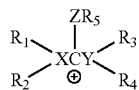 (1)

In the formula, $R_1$ to $R_5$ may be the same as or different from each other and each represents an H, a halogen, or a $C_1$ to $C_{10}$ (i.e. number of carbon from 1 to 10) alkyl group, cycloalkyl group, heterocyclic group, aryl group or alkoxyalkyl group; X and Y may be the same as or different from each other and each represents an N or a P; and Z represents an S or an O.

DETAILED DESCRIPTION OF THE INVENTION

As the counter ion to the above formula (1), at least one anion selected from the group consisting of $(CF_3SO_2)_2N^-$, $CF_3SO_3^-$, $CF_3CH_2SO_3^-$, $CF_3COO^-$, $PF_6^-$, $BF_4^-$, $SbF_6^-$, $(CN)_2N^-$, $SO_4^{2-}$, $HSO_4^-$, $NO_3^-$, $F^-$, $Cl^-$, $Br^-$ and $I^-$ is preferable; by combining this with a cation as described above, an ionic liquid exhibiting a liquid state at below 20° C. can be formed.

Regarding the cation of the formula (1), the ionic liquid is preferably one in which $R_1$ to $R_5$ in the formula (1) may be the same as or different from each other and each represents a $C_1$ to $C_{10}$ (i.e. number of carbons from 1 to 10) straight chain or branched alkyl group, and moreover the ionic liquid is preferably one in which X and Y in the formula (1) each represents an N.

The ionic liquid is more preferably one in which $R_1$ to $R_5$ in the formula (1) may be the same as or different from each other and each represents a $C_1$ to $C_5$ (i.e. number of carbons from 1 to 5) straight chain or branched alkyl group, X and Y each represents an N.

Moreover, the ionic liquid is yet more preferably one in which $R_1$ to $R_4$ in the formula (1) each represents a methyl group, $R_5$ represents an ethyl group, and the anion that is the counter ion is $(CF_3SO_2)_2N^-$, or one in which $R_1$ to $R_4$ in the formula (1) each represents a methyl group, $R_5$ represents a propyl group, and the anion that is the counter ion is $(CF_3SO_2)_2N^-$.

Moreover, the present inventors discovered that an ionic liquid as described above is a stable liquid having a good conductivity as required of an electrolyte or electrolyte additive for an electrical storage device, and can thus be used as a material in a lithium battery, a double layer capacitor, a dye-sensitized solar cell or the like. That is, the ionic liquids of the present invention have remarkable properties, exhibiting a liquid format below 20° C., and having a conductivity at 25° C. of 0.01 to 1.0 $Sm^{-1}$.

According to the present invention, there can be provided ionic liquids that have a good conductivity, and maintain a stable liquid state over a broad temperature range down to a low temperature, i.e. at or below 20° C., in some cases at or below −30° C.

Moreover, due to being a stable liquid from low temperatures to high temperatures, the ionic liquids provided by the present invention are suitable as electrolytes or electrolyte additives for electrical storage devices such as lithium batteries, double layer capacitors or dye-sensitized solar cells. Furthermore, the ionic liquids of the present invention are fire-resistant, having a property of hardly exhibiting a vapor pressure, and hence are also suitable for use as green solvents that are safe and environmentally friendly as a substitute for volatile organic solvents.

The cation represented by the formula (1) has been represented as a methyl cation (methylium) in which the positive electrical charge is placed on the carbon, but depending on the types of the hetero atoms represented by X, Y and Z, it is thought that the positive electrical charge will be delocalized through the molecule.

An ionic liquid (4) containing a cation represented by the formula (1) can be synthesized through the two-step reaction shown in the reaction formula below. First, a raw material having a structure represented by (2) is dissolved in a reaction solvent such as tetrahydrofuran, 1 to 1.5 equivalents of an organic compound $R_5Q$ having a substituent Q ($R_5$ represents a $C_1$ to $C_{10}$ straight chain or branched alkyl group; and Q represents a halogen, $HSO_4$ or $NO_3$) is added dropwise thereinto, and stirring is carried out for 18 to 36 hours at 20 to 100° C., thus adding $R_5$ to Z, and hence producing a salt (3) containing (1). Next, (3) is washed with diethyl ether or the like, then vacuum drying is carried out, and then a salt or compound AB having a desired anion and (3) are mixed together in equal amounts in water or an organic solvent at room temperature (heating may be required in some cases), thus carrying out anion exchange, whereby the ionic liquid (4) can be obtained.

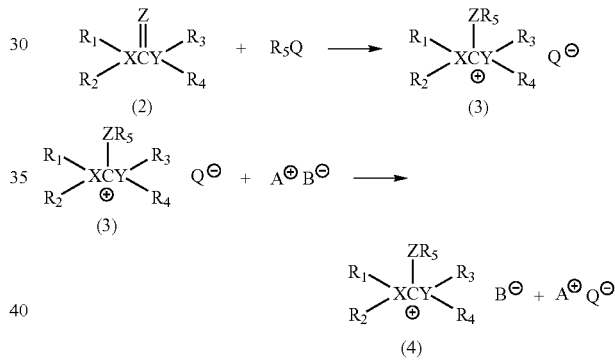

In the formulae, $R_1$ to $R_5$ each represents an H, or a $C_1$ to $C_{10}$ alkyl group, cycloalkyl group, heterocyclic group, aryl group or alkoxyalkyl group. Examples of the alkyl groups include straight chain or branched alkyl groups such as methyl, ethyl, propyl, isopropyl, n-butyl, isobutyl, sec-butyl, pentyl, hexyl, heptyl, octyl, nonyl or decyl. Moreover, such alkyl groups include alkyl groups having one or more halogens therein, and ones having unsaturated bonds such as alkenyl groups or alkynyl groups.

Examples of the above-mentioned cycloalkyl groups include cyclopropyl, cyclobutyl, cyclopentyl, cyclohexyl, cycloheptyl, cyclooctyl, cyclononyl and cyclodecyl. Moreover, such cycloalkyl groups include cycloalkyl groups having one or more halogens therein, and ones having unsaturated bonds such as cycloalkenyl groups or cycloalkynyl groups.

Moreover, examples of the heterocyclic groups include pyrrolidinyl, pyrrolinyl, imidazolidinyl, imidazolinyl, pyrazolidinyl, pyrazolinyl, piperidyl, piperazinyl, morpholinyl and thienyl groups. Moreover, such heterocyclic groups may contain one or more alkyl groups, alkoxy groups, hydroxyl groups, carboxyl groups, amino groups, alkylamino groups, dialkylamino groups, thiol groups, alkylthiol groups and/or halogens.

Examples of the above-mentioned aryl groups include phenyl, cumenyl, mesityl, tolyl and xylyl groups. Moreover, such aryl groups may contain one or more alkoxy groups, hydroxyl groups, carboxyl groups, amino groups, alkylamino groups, dialkylamino groups, thiol groups, alkylthiol groups and/or halogens.

Examples of the alkoxyalkyl groups include methoxymethyl, methoxyethyl, ethoxymethyl and ethoxyethyl.

Furthermore, as the hetero atoms represented by X, Y and Z in the formula (1), X and Y each represents an N or a P, and Z represents an S or an O.

On the other hand, examples of the anion that is the counter ion to (1) are $(CF_3SO_2)_2N^-$, $CF_3SO_3^-$, $CF_3CH_2SO_3^-$, $CF_3COO^-$, $PF_6^-$, $BF_4^-$, $SbF_6^-$, $(CN)_2N^-$, $SO_4^{2-}$ and $NO_3^-$. Moreover, a combination of a plurality of such anions may be used.

Examples of the compound AB include $LiN(CF_3SO_2)_2$, $NaN(CF_3SO_2)_2$, $KN(CF_3SO_2)_2$, $CF_3SO_3Li$, $CF_3SO_3Na$, $CF_3SO_3K$, $CF_3CH_2SO_3Li$, $CF_3CH_2SO_3Na$, $CF_3CH_2SO_3K$, $CF_3COOLi$, $CF_3COONa$, $CF_3COOK$, $LiPF_6$, $NaPF_6$, $KPF_6$, $LiBF_4$, $NaBF_4$, $KBF_4$, $LiSbF_6$, $NaSbF_6$, $KSbF_6$, $NaN(CN)_2$, $AgN(CN)_2$, $Na_2SO_4$, $K_2SO_4$, $NaNO_3$ and $KNO_3$, but there is no limitation to these compounds.

The ionic liquid containing the cation represented by the formula (1) can be also synthesized by an alkylation reaction with an ester. For example, a raw material having the structure represented by formula (2) and an ester $R_5W$ having a substituent W are mixed and stirred at a reaction temperature of 0 to 100° C. for 1 to 100 hours to add $R_5$ to Z and produce a crude salt (5) containing formula (1). Then, the crude salt (5) is washed with diethyl ether or the like and then vacuum-dried to obtain a purified ionic liquid (5). Moreover, an ionic liquid or a compound having an intended anion and the purified salt (5) are mixed and stirred in water or an organic solvent to conduct an anion exchange and selectively obtain an ionic liquid having a different anion.

As the $R_5W$ in the above formula, a dialkyl sulfate ester, a dialkyl sulfonate ester, a dialkyl carbonate ester, a trialkyl phosphate ester, an alkyl mono- or poly-fluoroalkylsulfonate, an alkyl perfluoroalkylsulfonate, an alkyl mono- or poly-fluorocarbonate, an alkyl perfluorocarbonate etc. may be proposed.

EXAMPLES

Following is a detailed description of the present invention based on Examples; however, the present invention is not limited to these Examples.

Example 1

(a) Preparation of bis(dimethylamino)ethylthiomethyliumiodide

A three-necked round bottomed flask equipped with a reflux condenser, a dropping funnel and a stirrer was purged with nitrogen, 11.5 g (86.9 mmol) of tetramethylthiourea and 250 ml of tetrahydrofuran were put in, and then 18.5 g (130 mmol) of iodoethane was added dropwise thereinto while stirring. The mixture was refluxed for 18 hours under nitrogen, and then the white crystals obtained were recovered by decantation, washed with diethyl ether, and then vacuum dried for 5 hours at 80° C., whereby 24.5 g (yield 98%) of bis(dimethylamino)ethylthiomethylium iodide was obtained.

Identification of the compound was carried out using a nuclear magnetic resonance analyzer (Varian Gemini 200 NMR Spectrometer made by Varian Japan Ltd.). The spectral data is shown below.

$^1$H-NMR (200 MHz, solvent: $D_2O$, standard substance: sodium 4,4-dimethyl-4-silapentanesulfonate)

δ 3.29 (s, 12H)
3.04 (q, 2H)
1.32 (t, 3H).

The structural formula is shown below.

(b) Preparation of bis(dimethylamino)ethylthiomethylium bis(trifluoromethanesulfonyl)imide 21.1 g (73.3 mmol) of the bis(dimethylamino)ethylthiomethylium iodide obtained in (a) was dissolved in 300 ml of pure water, and the resulting solution was added to an aqueous solution of 21.0 g (73.3 mmol) of lithium bis(trifluoromethanesulfonyl) imide in 50 ml of pure water, and stirring was carried out for 60 minutes, thus obtaining a hydrophobic colorless transparent liquid. The hydrophobic liquid obtained was washed several times with pure water, and then extraction was carried out with dichloromethane, the extract was concentrated, and then vacuum drying was carried out for 10 hours at 80° C., whereby 31.6 g (yield 98%) of a colorless transparent liquid at room temperature was obtained. Identification of the compound was carried out using a nuclear magnetic resonance analyzer, thus verifying that the compound was that aimed for, i.e. bis(dimethylamino)ethylthiomethylium bis(trifluoromethanesulfonyl)imide. The spectral data is shown below.

$^1$H-NMR (200 MHz, solvent: acetone-d6, standard substance: tetramethylsilane)

δ 3.45 (s, 12H)
3.20 (q, 2H)
1.38 (t, 3H)

$^{19}$F-NMR (188 MHz, solvent: acetone-d6, standard substance: $CFCl_3$)

δ −80.41 (s, 6F)

The structural formula is shown below.

Melting point measurement was carried out using a differential scanning calorimeter (DSC8230 made by Rigaku Corporation). A glass transition temperature of −81.2° C. was exhibited, but a peak corresponding to the melting point was not observed. The state was thus observed visually over time using a low temperature thermostatic bath, whereupon it was verified that the liquid state was maintained even after leaving for one week at a low temperature of −30° C. The decomposition onset temperature was measured using a thermogravimetric analyzer (TG8120 made by Rigaku Corporation). The weight loss onset temperature when measured with a heating rate of 10° C./min was 273° C. These results show that the salt of the present example maintains a stable liquid state over a broad temperature range from a temperature of or below −30° C. up to 273° C. Moreover, conductivity measurement was carried out using an electrical impedance method (HZ-3000 electrochemical measurement system made by Hokuto Denko Corporation). The conductivity at 25° C. was 0.4 $Sm^{-1}$.

Example 2

(a) Preparation of bis(dimethylamino)propylthiomethylium iodide

A three-necked round bottomed flask equipped with a reflux condenser, a dropping funnel and a stirrer was purged with nitrogen, 11.5 g (86.9 mmol) of tetramethylthiourea and 260 ml of tetrahydrofuran were put in, and then 22.1 g (130 mmol) of iodopropane was added dropwise thereinto while stirring. The mixture was refluxed for 35 hours under nitrogen, and then the white crystals obtained were recovered by decantation, washed with diethyl ether, and then vacuum dried for 5 hours at 80° C., whereby 23.3 g (yield 89%) of bis(dimethylamino)propylthiomethylium iodide was obtained. Identification of the compound was carried out using a nuclear magnetic resonance analyzer. The spectral data is shown below.

$^1$H-NMR (200 MHz, solvent: $D_2O$, standard substance: sodium 4,4-dimethyl-4-silapentanesulfonate)

δ 3.29 (s, 12H)

3.01 (t, 2H)

1.70 (m, 2H)

1.01 (t, 3H)

The structural formula is shown below.

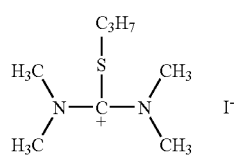

(b) Preparation of bis(dimethylamino)propylthiomethylium bis(trifluoromethanesulfonyl)imide 20.0 g (66.2 mmol) of the bis(dimethylamino) propylthiomethylium iodide obtained in (a) was dissolved in 300 ml of pure water, and the resulting solution was added to an aqueous solution of 19.0 g (66.2 mmol) of lithium bis(trifluoromethanesulfonyl)imide in 50 ml of pure water, and stirring was carried out for 60 minutes, thus obtaining a hydrophobic colorless transparent liquid. The hydrophobic liquid obtained was washed several times with pure water, and then extraction was carried out with dichloromethane, the extract was concentrated, and then vacuum drying was carried out for 10 hours at 80° C., whereby 26.4 g (yield 88%) of a colorless transparent liquid at room temperature was obtained. Identification of the compound was carried out using a nuclear magnetic resonance analyzer, thus verifying that the compound was that aimed for, i.e. bis(dimethylamino)propylthiomethylium bis(trifluoromethanesulfonyl)imide. The spectral data is shown below.

$^1$H-NMR (200 MHz, solvent: acetone-d6, standard substance: tetramethylsilane)

δ 3.44 (s, 12H)

3.16 (t, 2H)

1.75 (m, 2H)

1.04 (t, 3H)

$^{19}$F-NMR (188 MHz, solvent: acetone-d6, standard substance: $CFCl_3$)

δ −80.39 (s, 6F)

The structural formula is shown below.

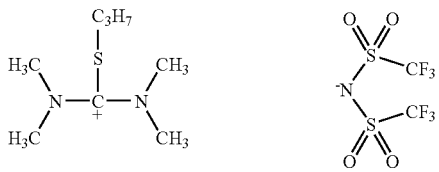

Measurement was carried out using a differential scanning calorimeter. A glass transition temperature of −78.7° C. was exhibited, but a peak corresponding to the melting point was not observed. The state was thus observed visually over time using a low temperature thermostatic bath, whereupon it was verified that the liquid state was maintained even after leaving for one week at a low temperature of −20° C. The weight loss onset temperature measured using a thermogravimetric analyzer with a heating rate of 10° C./min was 263° C. These results show that the salt of the present example maintains a stable liquid state over a broad temperature range from a temperature of or below −20° C. up to 263° C. Moreover, the conductivity at 25° C. was 0.3 $Sm^{-1}$.

Example 3

(a) Preparation of bis(methylamino)ethylthiomethylium iodide

A three-necked round bottomed flask equipped with a reflux condenser, a dropping funnel and a stirrer was purged with nitrogen, 10.4 g (100 mmol) of 1,3-dimethylthiourea and 300 ml of tetrahydrofuran were put in, and then 23.4 g (150 mmol) of iodoethane was added dropwise thereinto while stirring. The mixture was refluxed for 20 hours under nitrogen, and then the white crystals obtained were recovered by decantation, washed with diethyl ether, and then vacuum dried for 5 hours at 80° C., whereby 25.7 g (yield 99%) of bis(methylamino)ethylthiomethylium iodide was obtained. Identification of the compound was carried out using a nuclear magnetic resonance analyzer. The spectral data is shown below.

$^1$H-NMR (200 MHz, solvent: $D_2O$, standard substance: sodium 4,4-dimethyl-4-silapentanesulfonate)

δ 3.14 (q, 2H)

3.05 (s, 6H)

1.38 (t, 3H).

The structural formula is shown below.

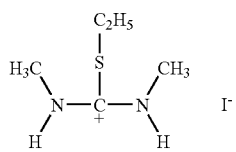

(b) Preparation of bis(methylamino)ethylthiomethylium bis(trifluoromethanesulfonyl)imide 21.9 g (84.4 mmol) of the bis(methylamino) ethylthiomethylium iodide obtained in (a) was dissolved in 50 ml of pure water, and the resulting solution was added to an aqueous solution of 24.2 g (84.4 mmol) of lithium bis(trifluoromethanesulfonyl)imide in 50 ml of pure water, and stirring was carried out for 60 minutes, thus obtaining a hydrophobic colorless transparent liquid. The hydrophobic liquid obtained was washed several times with pure water, and then extraction was carried out with dichloromethane, the extract was concentrated, and then vacuum drying was carried out for 10 hours at 80° C., whereby 33.9 g (yield 97%) of a colorless transparent liquid at room temperature was obtained. Identification of the compound was carried out using a nuclear magnetic resonance analyzer, thus verifying that the compound was that aimed for, i.e. bis(methylamino)ethylthiomethylium bis(trifluoromethanesulfonyl)imide. The spectral data is shown below.

$^1$H-NMR (200 MHz, solvent: acetone-d6, standard substance: tetramethylsilane)

δ 8.36 (s, 2H)

3.34 (q, 2H)

3.18 (s, 6H)

1.44 (t, 3H)

$^{19}$F-NMR (188 MHz, solvent: acetone-d6, standard substance: CFCl$_3$)

δ −80.42 (s, 6F)

The structural formula is shown below.

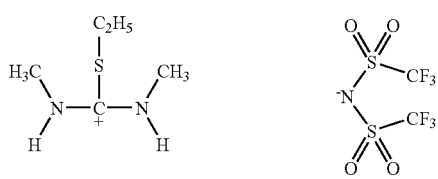

Measurement was carried out using a differential scanning calorimeter. The melting point was 19.2° C., the crystallization temperature was −23.6° C., and the glass transition temperature was −68.4° C. Through visual observation using a low temperature thermostatic bath, it was verified that the liquid state was maintained even after leaving for one week at 20° C. The weight loss onset temperature measured using a thermogravimetric analyzer with a heating rate of 10° C./min was 225° C. These results show that the salt of the present example maintains a stable liquid state over a broad temperature range from a temperature of or below 20° C. up to 225° C. Moreover, the conductivity at 25° C. was 0.2 Sm$^{-1}$.

Example 4

(a) Preparation of bis(dimethylamino)ethoxymethylium iodide

A 50 ml autoclave was purged with nitrogen, and 5.8 g (50 mmol) of teteramethylurea and 9.4 g (60 mmol) of iodoethane were put in. This mixture was heated at 100° C. for 8 hours and then cooled. The obtained white crystals were sufficiently washed with ether and then vacuum dried at 80° C. for 5 hours, whereby 11.6 g (yield 85%) of bis (dimethylamino) ethoxymethylium iodide was obtained.

The structural formula is shown below.

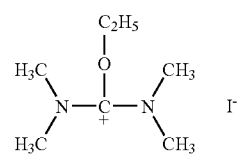

(b) Preparation of bis(dimethylamino)ethoxymethylium bis(trifluoromethanesulfonyl)imide 2.7 g (10 mmol) of bis (dimethylamino)ethoxymethylium iodide obtained in (a) was dissolved in 100 ml of pure water, and to this aqueous solution was added an aqueous solution of 2.9 g (10 mmol) of lithium bis(trifluoromethanesulfonyl) imide dissolved in 100 ml of pure water while stirring. Stirring was continued for 60 minutes to react, whereby a hydrophobic pale yellow transparent liquid was obtained. The obtained hydrophobic liquid was washed with pure water for 2 to 3 times, and then extracted with dichloromethane and purified by alumina column, whereby a colorless liquid was obtained. The extract was concentrated and then vacuum dried at 80° C. for 10 hours, whereby 4.0 g (yield 94%) of a colorless transparent liquid at room temperature was obtained. Identification of the compound was carried out using a nuclear magnetic resonance analyzer (Varian Gemini 200 NMR Spectrometer made by Varian Japan Ltd.), thus verifying that the compound was that aimed for, i.e. bis(dimethylamino)ethoxymethylium bis(trifluoromethanesulfonyl) imide. The spectral data is shown below.

$^1$H-NMR (200 MHz, solvent: acetone-d6, standard substance: tetramethylsilane)

δ 4.57 (q, 2H)

3.23 (s, 12H)

1.47 (t, 3H)

$^{19}$F-NMR (188 MHz, solvent: acetone-d6, standard substance: CFCl$_3$)

δ −79.91 (s, 6F).

The structural formula is shown below.

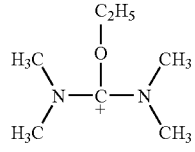 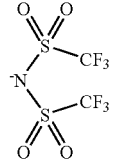

(c) Preparation of ethyl bis(dimethylamino)ethoxymethyliumsulfate

A three-necked round bottomed flask equipped with a reflux condenser, a dropping funnel and a stirrer was purged with nitrogen, 29.0 g (250 mmol) of tetramethylurea was put in, and then 77.1 g (500 mmol) of diethyl sulfate was added dropwise thereinto while stirring. The mixture was stirred at 50° C. for 72 hours to react under nitrogen, whereby a pale yellow transparent liquid was obtained. This liquid was sufficiently washed with ether and then vacuum dried at 60° C. for 5 hours, whereby 59.3 g (yield 87%) of ethyl bis(dimethylamino)ethoxymethyliumsulfate was obtained. Identification of the compound was carried out using a nuclear magnetic resonance analyzer (Varian Gemini 200 NMR Spectrometer made by Varian Japan Ltd.). The spectral data is shown below.

$^1$H-NMR (200 MHz, solvent: acetone-d6, standard substance: tetramethylsilane)

δ 4.56 (q, 2H)
3.87 (q, 2H)
3.21 (s, 12H)
1.45 (t, 3H)
1.15 (t, 3H)

The structural formula is shown below.

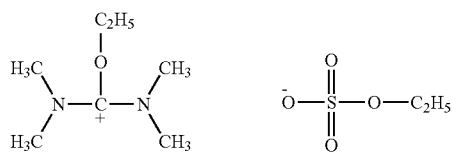

(d) Preparation of bis(dimethylamino)ethoxymethylium bis(trifluoromethanesulfonyl)imide 23.0 g (85.0 mmol) of ethyl bis(dimethylamino)ethoxymethyliumsulfate obtained in (c) was dissolved in 100 ml of pure water, and to this aqueous solution was added an aqueous solution of 24.4 g (85.0 mmol) of lithium bis(trifluoromethanesulfonyl)imide dissolved in 100 ml of pure water while stirring. Stirring was continued for 60 minutes to react, whereby a hydrophobic pale yellow transparent liquid was obtained. The obtained hydrophobic liquid was washed with pure water for 2 to 3 times, and then extracted with dichloromethane and purified by alumina column, whereby a colorless transparent liquid was obtained. The extract was concentrated and then vacuum dried at 80° C. for 10 hours, whereby 32.5 g (yield 90%) of a colorless transparent liquid at room temperature was obtained. Identification of the compound was carried out using a nuclear magnetic resonance analyzer (Varian Gemini 200 NMR Spectrometer made by Varian Japan Ltd.), thus verifying that the compound was that aimed for, i.e. bis(dimethylamino)ethoxymethylium bis(trifluoromethanesulfonyl)imide. The spectral data is shown below.

$^1$H-NMR (200 MHz, solvent: acetone-d6, standard substance: tetramethylsilane)

δ 4.57 (q, 2H)
3.23 (s, 12H)
1.47 (t, 3H)

$^{19}$F-NMR (188 MHz, solvent: acetone-d6, standard substance: CFCl$_3$)

δ −79.91 (s, 6F).

The structural formula is shown below.

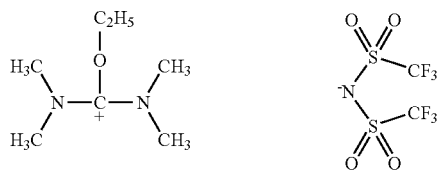

The melting point was measured using a differential scanning calorimeter (DSC8230 made by Shimadzu Corp.). The melting point was 14.2° C. and the crystallization temperature was −36.7° C. Through visual observation using a low temperature thermostatic bath, it was verified that the liquid state was maintained even after leaving for one week at low temperatures of −15° C. The decomposition onset temperature was measured using a thermogravimetric analyzer (TG8120made by Rigaku Corporation) The weight loss onset temperature measured at a heating rate of 10° C./min was 155° C. These results show that the salt of the present example maintains a stable liquid state over a broad temperature range from a temperature of or below −15° C. up to 155° C. Moreover, the conductivity at 25° C. measured using an electrical impedance method (HZ-3000 electrochemical measurement system made by Hokuto Denko Corporation) was 0.55 Sm$^{-1}$.

Example 5

Preparation of bis(dimethylamino)ethoxymethylium hexafluorophosphate 18.9 g (70.0 mmol) of bis(dimethylamino)ethoxymethylium ethyl sulfate obtained in Example 4 (c) was dissolved in 100 ml of pure water, and to this aqueous solution was added an aqueous solution of 10.6 g (70.0 mmol) of lithium hexafluorophosphate dissolved in 100 ml of pure water while stirring. Stirring was continued for 60 minutes to react, whereby a hydrophobic pale yellow transparent liquid was obtained. The obtained hydrophobic liquid was washed with pure water for 2 to 3 times, and then extracted with dichloromethane and purified by alumina column, whereby a colorless transparent liquid was obtained. The extract was concentrated, and then vacuum dried at 80° C. for, whereby 14.5 g (yield 71%) of a colorless transparent liquid at room temperature was obtained. Identification of the compound was carried out using a nuclear magnetic resonance analyzer (Varian Gemini 200 NMR Spectrometer made by Varian Japan Ltd.), thus verifying that the compound was that aimed for, i.e. bis(dimethylamino)ethoxymethylium hexafluorophosphate. The spectral data is shown below.

$^1$H-NMR (200 MHz, solvent: acetone-d6, standard substance: tetramethylsilane)

δ 4.56 (q, 2H)
3.22 (s, 12H)
1.47 (t, 3H)

$^{19}$F-NMR 188 MHz, solvent: acetone-d6, standard substance: CFCl$_3$)

δ −71.38 (s, 3F)
−73.89 (s, 3F).

The structural formula is shown below.

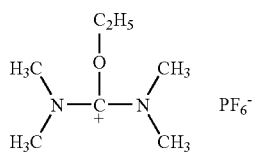

The melting point was measured using a differential scanning calorimeter (DSC8230 made by Shimadzu Corp.). The melting point was 48.3° C. and the crystallization temperature was −8.1° C. Through visual observation using a low temperature thermostatic bath, it was verified that the liquid state was maintained even after leaving for one week at 20° C. The decomposition onset temperature was measured using a thermogravimetric analyzer (TG8120 made by Rigaku Corporation). The weight loss onset temperature measured at a heating rate of 10° C./min was 195° C. These results show that the salt of the present example maintains a stable liquid state over a broad temperature range from a temperature of or below 20° C. up to 195° C. Moreover, the conductivity at 25° C. measured using an electrical impedance method (HZ-3000 electrochemical measurement system made by Hokuto Denko Corporation) was 0.19 $Sm^{-1}$.

Example 6

(a) Preparation of bis(dimethylamino)propoxymethylium iodide

A 50 ml autoclave was purged with nitrogen, and 5.8 g (50 mmol) of tetramethylurea and 17.0 g (100 mmol) of iodopropane were put in. This mixture was heated at 100° C. for 24 hours, and the cooled. The obtained white crystals were sufficiently washed with ether and then vacuum dried at 80° C. for 5 hours, whereby 6.4 g (yield 45%) of bis(dimethylamino)propoxymethylium iodide was obtained.

The structural formula is shown below.

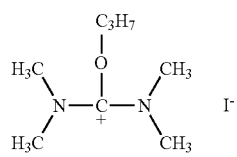

(b) Preparation of bis(dimethylamino)propoxymethylimu bis(trifluoromethaenesulfonyl)imide 10.3 g (35.9 mmol) of bis(dimethylamino)propoxymethylium iodide obtained in (a) was dissolved in 100 ml of pure water, and to this aqueous solution was added an aqueous solution of 10.3 g (35.9 mmol) of lithium bis(trifluoromethanesulfonyl)imide dissolved in 100 ml of pure water while stirring. Stirring was continued for 60 minutes to react, whereby a hydrophobic pale yellow transparent liquid was obtained. The obtained hydrophobic liquid was washed with pure water for 2 to 3 times, and then extracted with dichloromethane and purified by alumina column, whereby a colorless transparent liquid was obtained. The extract was concentrated and then vacuum dried at 80° C. for 10 hours, whereby 15.0 g (yield 95%) of a colorless transparent liquid at room temperature was obtained. Identification of the compound was carried out using a nuclear magnetic resonance analyzer (Varian Gemini 200 NMR Spectrometer made by Varian Japan Ltd.), thus verifying that the compound was that aimed for, i.e. bis(dimethylamino)propoxymethylium bis(trifluoromethanesulfonyl)imide. The spectral data is shown below.

$^1$H-NMR (200 MHz, solvent: acetone-d6, standard substance: tetramethylsilane)

δ 4.48 (t, 2H)

3.24 (s, 12H)

1.95-1.83 (m, 2H)

1.03 (t, 3H)

$^{19}$F-NMR (188 MHz, solvent: acetone-d6, standard substance: $CFCl_3$)

δ −79.92 (s, 6F).

The structural formula is shown below.

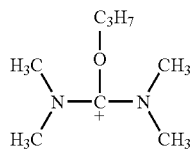 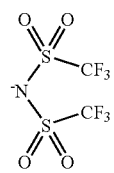

(c) Preparation of propyl bis(dimethylamino)propoxymethyliumsulfate

A three-necked round bottomed flask equipped with a reflux condenser, a dropping funnel and a stirrer was purged with nitrogen, 9.3 g (80 mmol) of tetramethylurea was put in, and then 25.5 g (140 mmol) of dipropyl sulfate was added dropwise thereinto while stirring. The mixture was stirred to react at 50° C. for 95 hours under nitrogen, whereby a pale yellow transparent liquid was obtained. This liquid was sufficiently washed with ether and then vacuum dried at 60° C. for 5 hours, whereby 13.3g (yield 56%) of propyl bis(dimethylamino)propoxymethyliumsulfate was obtained. Identification of the compound was carried out using a nuclear magnetic resonance analyzer (Varian Gemini 200 NMR Spectrometer made by Varian Japan Ltd.). The spectral data is shown below.

$^1$H-NMR (200 MHz, solvent: acetone-d6, standard substance: tetramethylsilane)

δ 4.47 (t, 2H)

3.80 (t, 2H)

3.22 (s, 12H)

1.94-1.82 (m, 2H)

1.61-1.51 (m, 2H)

1.02 (t, 3H)

0.90 (t, 3H)

The structural formula is shown below.

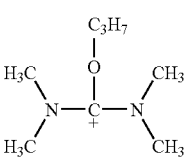 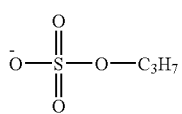

(d) Preparation of bis(dimethylamino)propoxymethylium bis(trifluoromethaenesulfonyl)imide 11.8 g (40.0 mmol) of propyl bis(dimethylamino)propoxymethyliumsulfate obtained in (c) was dissolved in 100 ml of pure water, and to this aqueous solution was added an aqueous solution of 11.4 g (40.0 mmol) of lithium bis(trifluoromethanesulfonyl)imide dissolved in100 ml of pure water while stirring. Stirring was continued for 60 minutes to react, whereby a hydrophobic pale yellow transparent liquid was obtained. The obtained hydrophobic liquid was washed with pure water for 2 to 3 times, and then extracted with dichloromethane and purified by alumina column, whereby a colorless transparent liquid was obtained. The extract was concentrated and then vacuum dried at 80° C. for 10 hours, whereby (yield 90%) of a colorless transparent liquid at room temperature was obtained. Identification of the compound was carried out using a nuclear magnetic resonance analyzer (Varian Gemini 200 NMR Spectrometer made by Varian Japan Ltd.), thus verifying that the compound was that aimed for, i.e. bis(dimethylamino)propoxymethylium bis(trifluoromethanesulfonyl)imide. The spectral data is shown below.

$^1$H-NMR (200 MHz, solvent: acetone-d6, standard substance: tetramethylsilane)

δ 4.48 (t, 2H)

3.24 (s, 12H)

1.95-1.83 (m, 2H)

1.03 (t, 3H)

$^{19}$F-NMR (188 MHz, solvent: acetone-d6, standard substance: CFCl$_3$)

δ −79.92 (s, 6F).

The structural formula is shown below.

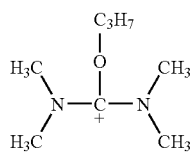 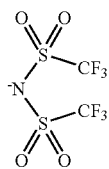

The melting point was measured using a differential scanning calorimeter (DSC8230 made by Shimadzu Corp.). A glass transition temperature of −83.2° C. was exhibited, but a peak corresponding to the melting point was not observed. The state was thus observed visually using a low temperature thermostatic bath, whereupon it was verified that the liquid state was maintained even after leaving for one week at a low temperature of −30° C. The decomposition on set temperature was measured using a thermogravimetric analyzer (TG8120 made by Rigaku Corporation). The weight loss onset temperature measured at a heating rate of 10° C./min was 166° C. These results show that the salt of the present example maintains a stable liquid state over a broad temperature range from a temperature of or below −30° C. up to 166° C. Moreover, the conductivity at 25° C. measured using an electrical impedance method (HZ-3000 electrochemical measurement system made by Hokuto Denko Corporation) was 0.41 Sm$^{-1}$.

The properties of the ionic liquids obtained in Examples 1 to 6 are shown in Table 1.

| | | | | DSC measurement data | | | | |
|---|---|---|---|---|---|---|---|---|
| Example | Cation | Anion | Melting point (° C.) | Glass transition temperature (° C.) | Crystallization temperature (° C.) | Visually observed melting point (° C.) | Conductivity at 25° C. (Sm$^{-1}$) | Decomposition onset temperature (° C.) |
| 1 | [C$_2$H$_5$ cation structure] | [NTf$_2$ anion] | — | −81.2 | — | −30° C. or less | 0.4$^-$ | 273 |
| 2 | [C$_3$H$_7$ cation structure] | [NTf$_2$ anion] | — | −78.7 | — | −24° C. to −30° C. | 0.3 | 263 |
| 3 | [C$_2$H$_5$ cation structure with NH] | [NTf$_2$ anion] | 19.2 | −68.4 | −23.6 | 10° C. to 20° C. | 0.2 | 225 |

-continued

| | | | | DSC measurement data | | | | |
|---|---|---|---|---|---|---|---|---|
| Example | Cation | Anion | Melting point (° C.) | Glass transition temperature (° C.) | Crystallization temperature (° C.) | Visually observed melting point (° C.) | Conductivity at 25° C. (Sm$^{-1}$) | Decomposition onset temperature (° C.) |
| 4 |  | O=S(CF$_3$)(=O)-N-S(=O)(=O)CF$_3$ | 14.2 | — | −36.7 | −15° C. to −20° C. | 0.55 | 155 |
| 5 | (same cation as 4 shown) | PF$_6^-$ | 48.3 | — | −8.1 | 10° C. to 20° C. | 0.19 | 195 |
| 6 |  | O=S(CF$_3$)(=O)-N-S(=O)(=O)CF$_3$ | — | −83.2 | — | −30° C. or less | 0.41 | 166 |

Note that the ionic liquids obbtained in Examples 1 to 6 were all hydrophobic.

The invention claimed is:

1. An ionic liquid comprising an organic compound represented by the following formula (1) as a cation:

$$\begin{array}{c} ZR_5 \\ R_1 \diagdown \mid \diagup R_3 \\ XCY \\ R_2 \diagup \oplus \diagdown R_4 \end{array} \quad (1)$$

in which $R_1$ to $R_5$ may be the same as or different from each other and each represents an H, a halogen, or a $C_1$ to $C_{10}$ alkyl group, cycloalkyl group, heterocyclic group, aryl group or alkoxyalkyl group; X and Y may be the same as or different from each other and each represents an N or a P; and Z represents an S or an O.

2. An ionic liquid comprising a cation and an anion, wherein the cation comprises at least one selected from the group consisting of cations represented by the following formula (1):

$$\begin{array}{c} ZR_5 \\ R_1 \diagdown \mid \diagup R_3 \\ XCY \\ R_2 \diagup \oplus \diagdown R_4 \end{array} \quad (1)$$

in the formula, $R_1$ to $R_5$ may be the same as or different from each other and each represents an H, a halogen, or a $C_1$ to $C_{10}$ alkyl group, cycloalkyl group, heterocyclic group, aryl group or alkoxyalkyl group; X and Y may be the same as or different from each other and each represents an N or a P; and Z represents an S or an O.

3. The ionic liquid according to claim 1, wherein the anion that is a counter ion to the compound of the formula (1) comprises at least one selected from the group consisting of $(CF_3SO_2)_2N^-$, $CF_3SO_3^-$, $CF_3CH_2SO_3^-$, $CF_3COO^-$, $PF_6^-$, $BF_4^-$, $SbF_6^-$, $(CN)_2N^-$, $SO_4^{2-}$, $HSO_4^-$, $NO_3^-$, $F^-$, $Cl^-$, $Br^-$ and $I^-$.

4. The ionic liquid according to claim 1, wherein $R_1$ to $R_5$ in the formula (1) may be the same as or different from each other and each represents a $C_1$ to $C_5$ straight chain or branched alkyl group.

5. The ionic liquid according to claim 1, wherein X and Y in the formula (1) each represents an N; and Z represents an S.

6. The ionic liquid according to claim 1, wherein the anion that is a counter ion to the compound of the formula (1) comprises at least one selected from the group consisting of $(CF_3SO_2)_2N^-$, $CF_3SO_3^-$, $CF_3CH_2SO_3^-$, $CF_3COO^-$, $PF_6^-$, $BF_4^-$, $SbF_6^-$, $(CN)_2N^-$, $SO_4^{2-}$, $HSO_4^-$, $NO_3^-$, $F^-$, $Cl^-$, $Br^-$ and $I^-$, and $R_1$ to $R_5$ in the formula (1) may be the same as or different from each other and each represents a $C_1$ to $C_5$ straight chain or branched alkyl group; X and Y each represents an N; and Z represents an S.

7. The ionic liquid according to claim 1, wherein $R_1$ to $R_4$ in the formula (1) each represents a methyl group; $R_5$ represents an ethyl group; and the anion that is the counter ion is $(CF_3SO_2)_2N^-$.

8. The ionic liquid according to claim 1, wherein $R_1$ to $R_4$ in the formula (1) each represents a methyl group; $R_5$ represents a propyl group; and the anion that is the counter ion is $(CF_3SO_2)_2N^-$.

9. A lithium battery comprising the ionic liquid according to claim 1.

10. A double layer capacitor comprising the ionic liquid according to claim 1.

11. A dye-sensitized solar cell comprising the ionic liquid according to claim 1.

12. A green solvent containing the ionic liquid according to claim 1.

13. A process for manufacturing the ionic liquid according to claim 1, comprising the step of reacting together an organic compound $R_5Q$, wherein $R_5$ represents a $C_1$ to $C_{10}$ straight chain or branched alkyl group; and Q represents a halogen, $HSO_4$ or $NO_3$, and a compound represented by the following formula (2), wherein $R_1$ to $R_4$ may be the same as or different from each other and each represents an H, a halogen, or a $C_1$ to $C_{10}$ straight chain or branched alkyl group, cycloalkyl group, heterocyclic group, aryl group or alkoxyalkyl group; X and Y may be the same as or different from each other and each represents an N or a P; and Z represents an S or an O), in accordance with the following reaction scheme while stirring at 20 to 100° C., thus producing a salt represented by the formula (3)

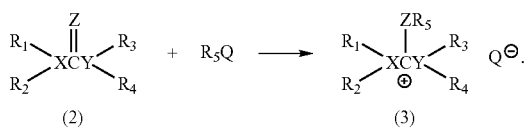

14. The process according to claim 13, wherein, after the reaction step of claim 13, the anion Q of the salt represented by the formula (3) and a compound AB, AB representing a compound selected from the group consisting of LiN($CF_3SO_2$)$_2$, NaN($CF_3SO_2$)$_2$, KN($CF_3SO_2$)$_2$, $CF_3SO_3$Li, $CF_3SO_3$Na, $CF_3SO_3$K, $CF_3CH_2SO_3$Li, $CF_3CH_2SO_3$Na, $CF_3CH_2SO_3$K, $CF_3$COOLi, $CF_3$COONa, $CF_3$COOK, LiPF$_6$, NaPF$_6$, KPF$_6$, LiBF$_4$, NaBF$_4$, KBF$_4$, LiSbF$_6$, NaSbF$_6$, KSbF$_6$, NaN(CN)$_2$, AgN(CN)$_2$, Na$_2$SO$_4$, K$_2$SO$_4$, NaNO$_3$ and KNO$_3$, are subjected to anion exchange through the reaction of the following reaction scheme, thus producing an ionic liquid represented by the formula (4)

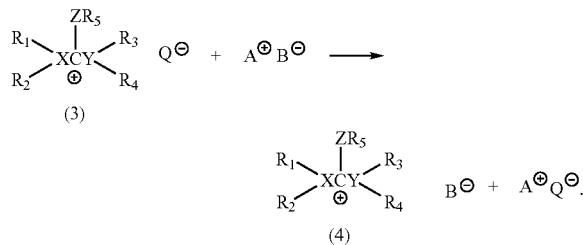

15. A process for manufacturing an ionic liquid comprising a cation and an anion, wherein the cation comprises at least one selected from the group consisting of cations represented by the following formula (1):

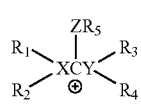

in the formula, $R_1$ to $R_5$ may be the same as or different from each other and each represents an H, a halogen, or a $C_1$ to $C_{10}$ alkyl group, cycloalkyl group, heterocyclic group, aryl group or alkoxyalkyl group; X and Y may be the same as or different from each other and each represents an N or a P; and Z represents an S or an O, comprising the step of reacting together an organic ester of the formula $R_5W$, wherein $R_5W$ is a dialkyl sulfate ester, a dialkyl sulfonate ester, a dialkyl carbonate ester, a trialkyl phosphate ester, an alkyl monofluoroalkylsulfonate, an alkyl polyfluoroalkylsulfonate or an alkyl perfluorocarbonate, and a compound represented by formula (2)

in accordance with the following reaction step while stirring at 20 to 100° C. to produce a salt represented by formula (5)

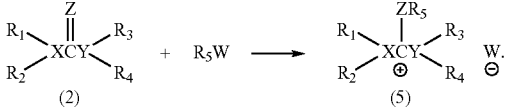

16. The process according to claim 15, wherein after the reaction step, the anion $W^\ominus$ and a compound AB, wherein AB is a compound selected from the group consisting of LiN($CF_3SO_2$)$_2$, NaN($CF_3SO_2$)$_2$, KN($CF_3SO_2$)$_2$, $CF_3CH_2SO_3$K, $CF_2$COOLi, $CF_3$COONa, $CF_3$COOK, LiPF$_6$, NaPF$_6$, KPF$_6$, LiBF$_4$, KBF$_4$, LiSbF$_6$, NaSbF$_6$, KSbF$_6$, NaN(CN)$_2$, AgN(CN)$_2$, Na$_2$SO$_4$, K$_2$SO$_4$, NaNO$_3$ and KNO$_3$, are subjected to anion exchange through the following reaction step to produce an ionic liquid of formula (4)

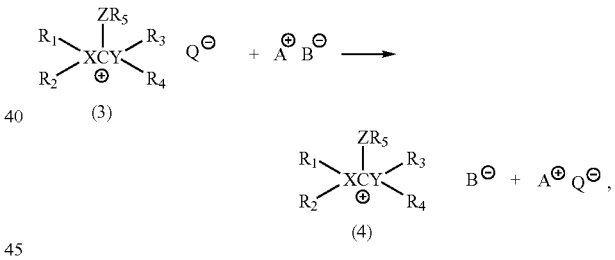

wherein Q is a halogen.

17. The ionic liquid according to claim 1, wherein $R_1$ to $R_4$ in the formula (1) each represents a methyl group; $R_5$ represents an ethyl group; and the anion that is the counter ion is $I^-$.

18. The ionic liquid according to claim 1, wherein $R_1$ to $R_4$ in the formula (1) each represents a methyl group; $R_5$ represents a propyl group; and the anion that is the counter ion is $I^-$.

19. The ionic liquid according to claim 1, wherein $R_1$ to $R_3$ in the formula (1) each represents a methyl group; $R_2$ and $R_4$ represents a H; and $R_5$ represents an ethyl group and the anion that is the counter ion is $I^-$.

20. The ionic liquid according to claim 1, wherein $R_1$ and $R_3$ in the formula (1) each represents a methyl group; $R_2$ and $R_4$ represents an H; and $R_5$ represents an ethyl group; and the anion that is the counter ion is $(CF_3SO_2)_2N^-$.

* * * * *